United States Patent [19]

Wagle et al.

[11] Patent Number: 5,055,296
[45] Date of Patent: Oct. 8, 1991

[54] METHOD OF TREATING CHRONIC FATIGUE SYNDROME

[76] Inventors: Sudhakar S. Wagle, 11505 N. River Rd., Mequon, Wis. 53092; S. Ken Tanaka, 3033 W. Renee Court, Mequon, Wis. 53092; Thomas Steinbach, No. 4 Bayou Shadows, Houston, Tex. 77024; Carl H. Lawyer, 10320 N. Fontainebleau Court, Mequon, Wis. 53092; William J. Hermann, Jr., 103 River Ridge Rd., Sealy, Tex. 77474

[21] Appl. No.: 228,364

[22] Filed: Aug. 4, 1988

[51] Int. Cl.$^5$ .......................................... A61K 35/407
[52] U.S. Cl. ..................... 424/553; 514/21; 514/885; 530/846
[58] Field of Search ............... 424/106, 553; 530/846; 514/21, 885

[56] References Cited

U.S. PATENT DOCUMENTS

| | | | |
|---|---|---|---|
| 3,788,510 | 12/1973 | Blonde | 424/106 |
| 4,148,788 | 4/1979 | Wang | 260/112.5 |
| 4,420,398 | 12/1983 | Castino | 210/641 |
| 4,426,324 | 1/1984 | Meienhofer | 260/112.5 |
| 4,428,938 | 1/1984 | Kisfaludy | 424/177 |
| 4,464,355 | 8/1984 | Fabricius | 424/101 |
| 4,468,379 | 8/1984 | Gottlieb | 424/101 |
| 4,537,878 | 8/1985 | Pltonikoff | 514/2 |
| 4,595,588 | 6/1986 | Baron et al. | 424/89 |
| 4,595,780 | 6/1986 | Ogata | 564/79 |
| 4,596,798 | 6/1986 | Shipman, Jr. | 514/183 |
| 4,598,095 | 7/1986 | Nishimura | 514/632 |
| 4,602,037 | 7/1986 | Seborm | 514/512 |
| 4,603,122 | 7/1986 | Blough | 514/23 |
| 4,603,219 | 7/1986 | Verheyden | 560/255 |
| 4,604,404 | 8/1986 | Munson, Jr. | 514/494 |
| 4,605,658 | 8/1986 | Holy | 514/261 |
| 4,605,659 | 8/1986 | Verheyden | 514/262 |
| 4,606,917 | 8/1986 | Eppstein | 424/85 |
| 4,609,661 | 9/1986 | Verheyden | 514/262 |
| 4,609,662 | 9/1986 | Krenitsky | 514/262 |
| 4,612,314 | 9/1986 | Verheyden | 514/261 |
| 4,614,651 | 9/1986 | Jarvis, Jr. | 424/85 |
| 4,614,731 | 9/1986 | Horecker | 514/12 |
| 4,617,304 | 10/1986 | Ashton | 514/261 |
| 4,621,140 | 11/1986 | Verheyden | 544/276 |
| 4,622,430 | 11/1986 | Dekker | 564/458 |
| 4,625,026 | 11/1986 | Kim | 544/249 |
| 4,626,524 | 12/1986 | Server | 514/13 |
| 4,628,063 | 12/1986 | Haines | 514/626 |
| 4,629,811 | 12/1986 | Dominianni | 564/99 |
| 4,631,149 | 12/1986 | Rinehart, Jr. | 540/546 |
| 4,644,055 | 2/1987 | Kettner | 530/330 |
| 4,668,660 | 5/1987 | Paessens | 514/383 |
| 4,670,437 | 6/1987 | Abdulla | 514/247 |
| 4,699,898 | 10/1987 | Gottlieb | 514/18 |
| 4,708,818 | 11/1987 | Montagnier | 435/5 |
| 4,710,380 | 12/1987 | Gottlieb | 424/101 |

OTHER PUBLICATIONS

Sandstrom et al., "Antiviral Therapy in AIDS" in *Drugs* 34(3):372–390, Sep. 1987.
Andrews et al., *JAMA*, 146, 1107 (1951).
Barksdale, *South. Med. Jour.*, 50, 1524 (1957).
Barksdale et al., *Virginia Medical Monthly*, 81, 321 (1954).
Barrock, *Medical Times*, 1, (Aug. 1958).
Boreen, *Minnesota Medicine*, 25, 276 (1942).
Burks, Jr., *Journal of the Louisiana Medical Society*, 106, 92 (1954).
Burks, Jr. and Knox, *Archives of Dermatology and Syphilology*, 70, 508 (1954).
Center for Disease Control, Dept. Health and Human Services, *Chronic Fatigue Syndrome*, Mar. 22, 1988.
Chase, *Wall Street Journal*, Apr. 28, 1988, at 14, at col. 1.

(List continued on next page.)

Primary Examiner—Douglas W. Robinson
Assistant Examiner—Jean C. Witz
Attorney, Agent, or Firm—Willian Brinks Olds Hofer Gilson & Lione

[57] ABSTRACT

A therapeutic method for treating viral infections and chronic fatigue syndrome. The method comprises administering a therapeutically-effective amount of a mammalian liver extract, the extract being characterized by being heat stable, insoluble in acetone and soluble in water.

4 Claims, 2 Drawing Sheets

OTHER PUBLICATIONS

Gaskell, *Brit. Med. J.*, 1037 (Jun. 11, 1949).
Gathings, *Am. J. Surgery*, 88, 429 (1954).
Gladner, *Ann. N.Y. Aca. Sci.*, 47.
Harris et al., *Oral Surgery*, 7, 239 (1954).
Hellinger et al., *JAMA*, 260, 971 (Aug. 19, 1988).
Heywood, *Clinical Medicine*, 3, 425 (1956).
Hjerten, *Archives of Biochemistry and Biophysics*, Suppl. 1, 147 (1962).
Hjerten and Mosbach, *Analytical Biochemistry*, 3, 109 (1962).
Holtman, *Oral Surgery*, 7, 12 (1954).
Judge, *Proc. Soc. Exptl. Biol. Med.*, 123, 299 (1966).
Kozelka and Marshall, *Clinical Medicine*, 3, 245 (1956).
Kutapressin— Drug Package Insert, Kremers–Urban.
Li et al., *Nature*, 219, 1163 (Sep. 14, 1968).
Li et al., *Proc. Soc. Exptl. Biol. Med.*, 114, 504 (1963).
Li et al., Proc. Soc. Exptl. Biol. Med., 109, 534 (1962).
Li et al., *J. Nat'l Cancer Inst.*, 41, 1249 (Nov. 1968).
Li et al., *Ann. N.Y. Acad. Sci.*, 130, 374 (1965).
Lichtenstein and Stillians, *Arch. Dermatology and Syphilology*, 45, 959 (1942).
Lubowe, *Clinical Medicine*, 59, 8 (1952).
Marshall et al., *Am. J. Surgery*, 90, 47 (1955).
Marshall, *Maryland State Med. J.*, (Jun. 1960).
Marshall, *Am. J. Surgery*, 84(6), 675 (1952).
Marshall and Schadeberg, *Wisconsin Medical Journal*, 49, 369 (1950).
Marshall and Schadeberg, *Indian J. Venerial Diseases*, 16, 89 (1950).
Marshall, *J. M. A. Alabama*, 255 (1944).
Marshall, *Mississippi Valley Med. J.*, 61, 172 (1939).
Marshall, *Med. World*, 57, 101 (1939).
Marshall, *Northwest Medicine*, 38, 467 (1939).
Marshall, *J. Invest. Derm.*, 2, 205 (1939).
Marshall, *Am. J. Surgery*, 448 (Oct. 1951).
Marshall, *Medical Times*, 79, 222 (1951).
Marshall, *Indian J. Veneral Diseases and Dermatology*, 20, 99 (1954).
Marshall, *The Journal–Lancet*, 60, 117 (1940).
Marshall, *Minnesota Medicine*, 25, 796 (1942).
Marshall, *Arizona Medicine*, 14(1), 11 (1957).
Marshall, *Mississippi Valley Med. J.*, 76, 199 (1954).
Mitchell–Heggs, *Brit. Med. J.*, 2, 1079 (1951).
Montefiori et al., *J. Clin. Micro.*, 26, 231 (Feb. 1988).
Montefiori and Mitchell, *Proc. Nat'l Acad. Sci U.S.A.*, 84(9), 2985 (May–1987).
National Formulary, vol. XII, p. 222.
National Formulary, vol. XI, pp. 192-194.
Nierman, *Journal of the Indiana State Medical Association*, 45, 497 (1952).
Osbahr et al., *Biochim. Biophys. Acta.*, 86, 535 (1964).
Pensky and Goldberg, *The Journal–Lancet*, 75(11), 490 (Nov. 1955).
Pensky and Goldberg, *New York State Journal of Medicine*, 53, 2238 (1953).
*Pharmacopeia of the United States*, 15, 379.
Pollner, *Medical World News*, 35 (Jun. 13, 1988).
Poole, *South Med. J.*, 50, 207 (1957).
Ruggieri, *Science*, 194, 491 (1976).
Schmeer and Huala, *Ann. N.Y. Acad. Sci.*, 118, 605 (1965).
Schmeer, *Science*, 144, 413 (1964).
Smith, *HIV and Other Highly Pathogenic Viruses*, Academic Press, Inc. (1988).
Stillians, *Mississippi Valley Medical Journal*, 64, 135 (1942).
Stokes and Sternberg, *Archives of Dermatology and Syphilology*, 40, 345 (1939).
Sutton, *Archives of Dermatology & Syphilology*, 18, 887 (1928).
Tewksbury and Stahmann, *Arch. Biochem. Biophys. (U.S.)*, 112, 453 (1965).
Tewksbury, *Archives Int'l de Pharmacodynamic et de Therapie*, 173, 426 (1968).
Tewksbury, *Dissertation Abstracts International–Part II*, 25/04, 2214 (1964).
Walters, *Ohio State Medical Journal*, 44, 697 (1948).
White, *The Letters of the International Correspondence Society of Allergists*, 19, 30 (1956).

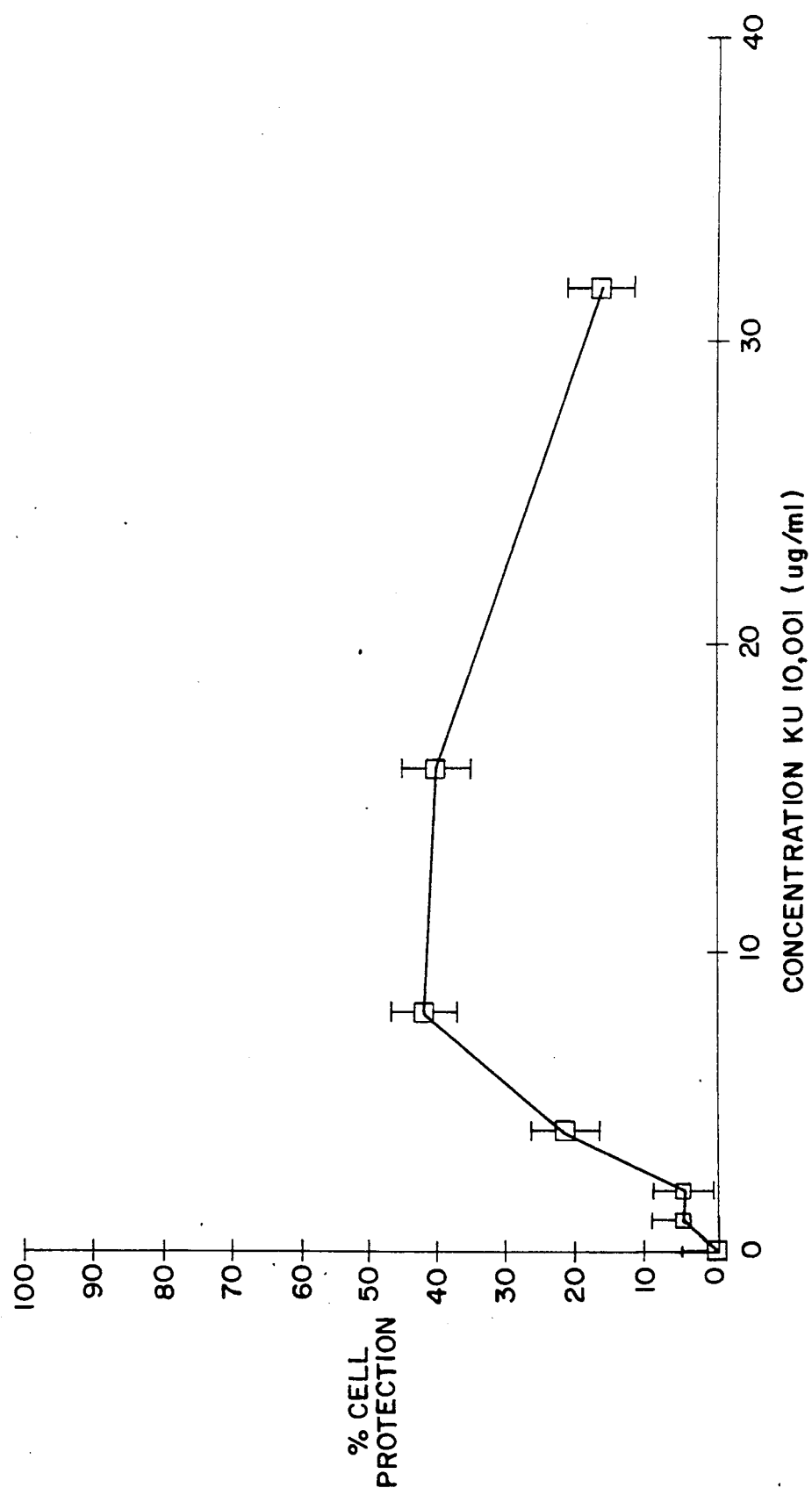

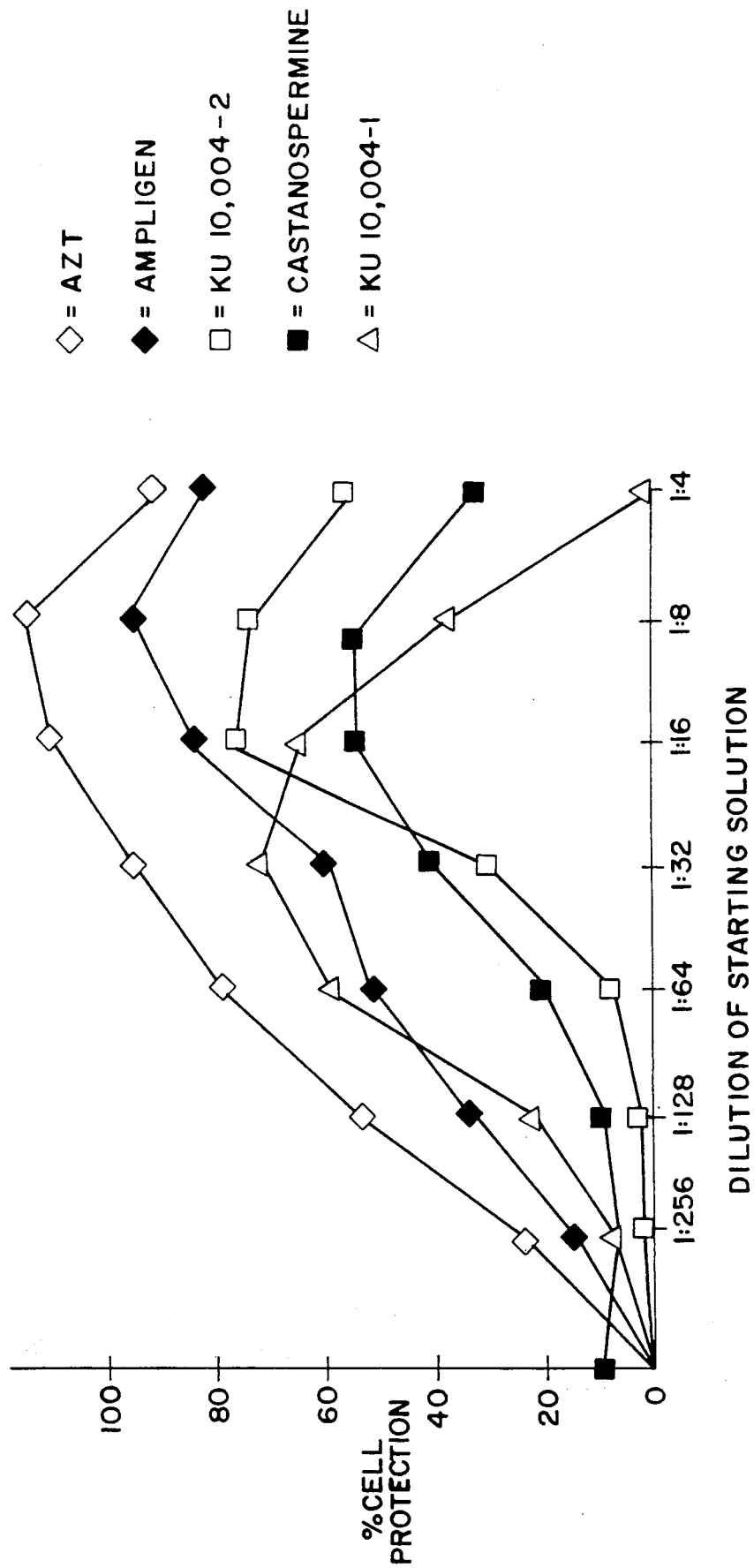

METHOD OF TREATING CHRONIC FATIGUE SYNDROME

FIELD OF THE INVENTION

The present invention is directed to a method of treating viral infections in mammals and to the discovery that a mammalian liver extract is efficacious in treating non-dermatologic viral infections. The present invention is also directed to a method of treating chronic fatigue syndrome with this same mammalian liver extract

BACKGROUND OF THE INVENTION

Although recent decades have been marked by rapid advances in the treatment of bacterial infections, there have not been comparable advances in the treatment of viral infections. Indeed, today, very few efficacious antiviral agents exist.

Those that are known either suffer from restricted or limited efficacy or are toxic. For instance, amantidine is known to prevent influenza, but must be given prior to infection to be effective. Acyclovir, while often effective in treating herpes virus infections, selects for resistant strains of virus. Also, acyclovir is not effective against many kinds of viruses, including retroviruses and even some herpes viruses, such as cytomegalovirus. Other antiviral agents, such as 3'-azido-3'-deoxythymidine (AZT), are toxic, their activity relying upon a relative, but not absolute, selectivity for viral processes.

Indirectly-acting anti-viral therapies, including interferon and interferon inducers, enhance cellular responsiveness to viral infection, allowing the cells to interfere with the infection process. However, interferon has not fulfilled the promise of early expectations and theory. Interferon inducers are relatively new to the field and their efficacy remains unproven.

Acquired immune deficiency syndrome (AIDS) and AIDS-related complex (ARC) are caused by human immuno-deficiency virus (HIV-1), a retrovirus. The HIV-1 virus infects immune, neural and other cells of its host. Eventually most people infected with HIV-1 become abnormally susceptible to a variety of serious opportunistic diseases as a result of the immune deficiency caused by the virus.

The current anti-HIV-1 drugs are either not effective or cause undesirable side effects. These drugs include AZT, 2',3'-dideoxy cytidine (ddCyd), interferon (IFN), mismatched double-stranded RNA (dsRNA) and amphotericin B. In particular, AZT, which has shown some promise in the treatment of AIDS, causes very serious side effects, such as bone marrow suppression, in a high proportion of patients. Also, the beneficial effects of AZT have been reported to abate in 12-18 months, and patients get new infections or develop toxic side effects. Chase, "Doctors and Patients Hope AZT Will Help Stave Off AIDS," *Wall Street Journal*, Apr. 28, 1988, at 14, col. 1.

An illness referred to as "chronic fatigue syndrome" (CFS) has been associated with an active Epstein-Barr virus infection as evidenced by significantly elevated titers of antibodies to the Epstein-Barr viral capsid antigen or early antigen and a deficiency of late-appearing antibodies in many patients suffering from CFS. However, in some patients, Epstein-Barr virus antibody patterns are not definitively abnormal, and some patients are seronegative. Accordingly, other agents may also be involved in the etiology of CFS. These other possible causes of CFS include cytomegalovirus, other viruses, chemical exposure, defects in the immune system, or severe allergies. Center for Disease Contral, Dept. Health and Human Services, *Chronic Fatigue Syndrome* Mar. 22, 1988 (hereinafter "*Centers for Disease Control*").

Patients suffering from CFS are chronically, sometimes severely, fatigued. They also show evidence of neurological and immunological dysfunctions.

To date, there is no known effective treatment for CFS. *Centers for Disease Control*. Several treatment studies are underway using gamma globulin and acyclovir. However, a study conducted by the National Institutes of Health indicates that acyclovir is no more effective than placebo in treating this illness. *Centers for Disease Control*.

Mammalian liver extract has been used for the treatment of a wide range of infectious and noninfectious dermatologic conditions, including acne vulgaris, *Journal.Invest Dermatology*, 2:205–218 (1939); first and second degree burns, *Mississippi Valley Medical Journal*, 76:199 (1954); sunburn, *Clinical Medicine*, 3:245 (1956); poison ivy dermatitis, *Clin. Med.*, 3:425 (1956) and Herpes zoster, *Southern Medical Journal*, 50:1524 (1957). The active principle and mechanism have not been described. Although some medical practitioners have used liver extract for the treatment of dermatologic conditions, it is not regarded as an antiviral or immune modulator agent even for skin therapy.

Mammalian liver extract has been reported to have bradykinin potentiating activity Tewksbury et al., *Arch. Biochem. Biophys.* (U.S.), 112, 453 (1965); Tewksbury, *Archives Int'l de Pharmacodynamie et de Therapie*, 173, 426 (1968); Tewksbury, *Dissertation Abstracts International-Part II*, Vol. 25/04, p. 2214 (1964). Further, one commercially-available liver extract (sold under the trademark KUTAPRESSIN by Kremers-Urban Co., Milwaukee, Wisconsin) exerts its action, according to product literature, only with respect to tissues that have been injured and when inflammation and edema are present.

BRIEF DESCRIPTION OF THE DRAWINGS

FIG. 1 illustrates the results of in vitro testing of the ability of a porcine liver extract to reduce the cytolysis of MT-2 lymphoblastoid cells upon infection with HIV-1 virus.

FIG. 2 illustrates the results of in vitro testing of the ability of AZT, ampligen, castanospermine and two preparations of porcine liver extract to reduce the cytolysis of MT-2 lymphoblastoid cells upon infection with HIV-1 virus.

SUMMARY OF THE INVENTION

It has now been discovered that a heat stable, acetone-insoluble, water-soluble mammalian liver extract is effective in the treatment of mammals infected with nondermatologic virus. This same mammalian liver extract has also been found to be effective in treating chronic fatigue syndrome (CFS). By "heat stable" is meant that the liver extract does not lose appreciable activity at temperatures at about 100° C. in water over 10 minutes.

DETAILED DESCRIPTION OF THE PRESENTLY PREFERRED EMBODIMENTS

The portion of mammalian liver extract that has been discovered to be effective in treating virus infections is the fraction which is heat stable, insoluble in acetone and soluble in water. The liver extract prepared according to the disclosure herein is free from high molecular weight protein, fatty acids, polysaccharides, and vitamins, and specifically is free from vitamin B-12, a vitamin naturally occurring in liver. This same liver extract has been used heretofore in treating skin conditions.

Preparation of the Liver Extract

The liver extract employed in the present invention is prepared by separating a fraction from mammalian livers, preferably porcine liver. The starting material may be a liver preparation as described in *Pharmacopeia of the United States*, Vol. 15, p. 379 (which describes a boiled liver extract suitable for parenteral use), in *National Formulary*, Vol. XII, p. 222 (which describes an aqueous solution of the thermostable fraction of mammalian liver) or in *National Formulary*, Vol. XI, p. 192–94 (which describes several thermostable liver preparations). Alternatively, the starting material may be fresh liver, frozen liver or a commercially-available liver preparation.

An acetone-insoluble fraction is separated from the starting material. This may be accomplished by admixing a large excess of acetone with the starting material which results in an acetone-insoluble fraction that is separated from the acetone. The treatment with acetone may be repeated. The acetone-insoluble fraction, after being separated from the acetone, is dissolved in water. Any remaining acetone is removed by, for example, distillation. The material effective in treating viral infections and CFS is contained in the water solution.

Alternatively, and preferably, before the acetone extraction, the starting material is suspended in water and incubated at room temperature. After incubation, the suspension is clarified by filtration, and the solution is passed over a cation exchange resin three times. The resulting resin-treated solution is then concentrated by evaporation, diluted with water, and centrifuged. The acetone-insoluble fraction is then separated from the supernatant by adding a large excess of acetone and further processed as described above.

The acetone-insoluble fraction may be further purified to remove the color pigments by treatment with activated charcoal. For example, the acetone-insoluble fraction may be dissolved in water and contacted with ammonia-activated charcoal.

A pharmaceutically-acceptable preservative usually is added to the water solution. For instance, phenol at from about 0.05 to about 1%, preferably about 0.5%, may be added.

The liver extract useful in the present invention may be prepared according to the following examples.

Example I

Preparation of Liver Extract

Liver Fraction I, described in National Formulary XI, page 193, was suspended in water to a concentration of 16% by weight. Phenol was added to a final concentration of 1%. The suspension was mixed and incubated for 7 days at room temperature. It was then clarified by filtration, evaporated to dryness by heating, and diluted to 8% solids by weight in water.

This aqueous solution was then passed three times through a cation exchange resin (sulfonated polystyrene). The resin-treated solution was clarified by filtration and concentrated to 40% total solids by weight by evaporation under vacuum at 65°–70° C. Cold water (5°–10° C.) was added (5 volumes of water to 7 volumes of liver solution) with mixing. The resultant solution was then centrifuged and the supernatant collected (Sharples-type centrifuge at 1 liter per minute). Phenol was added to a final concentration 0.5–1%.

This solution was adjusted to pH 6.0–7.0, with HCl or NaOH as necessary, clarified by filtration, and heated to 40° C. Then acetone was added (20–30 liters acetone per liter liver solution). The acetone-precipitable material was allowed to settle and most of the acetone was decanted off. The remaining suspension was incubated overnight at room temperature, after which the suspension was diluted to 10 liters with water, and the acetone was removed by distillation. Phenol and water were then added to give a final preparation containing 0.5% phenol and greater than 25 mg total solids per ml (herein designated "KU 10,000").

KU 10,000 was adjusted to pH 6.0–7.0 with HCl or NaOH, as necessary and diluted to 25 mg total solids per ml. with water (i.e., 2.5% by weight solids). The solution was then sterile filtered into suitable vials for use. This final solution is referred to herein as "KU 10,001".

Example II

Preparation of Liver Extract

A suitable liver extract may also be prepared as follows. Starting with a preparation of liver injection crude as described in the *Pharmacopeia of the United States*, 15th edition, page 379, a large excess of acetone (27 liters of acetone for each liter of liver) was added to precipitate an insoluble fraction. The acetone-insoluble fraction was separated from the acetone, and the foregoing step was repeated on the insoluble fraction. This was done for a total of three times. The insoluble fraction then was collected and dissolved in a minimum amount of water. The acetone was distilled away from the water solution.

Phenol was added to the water solution in an amount of 0.5% by volume as a preservative. The solution then was stored under refrigerated conditions for at least 30 days, during which time some insoluble materials were formed that were separated and removed by filtration or centrifugation and discarded. The solution was diluted with water so that the final solution contained 25 milligrams of liver extract solids per milliliter of water (i.e., 2.5% by weight solids). The pH was adjusted to about 7.0 by adding hydrochloric acid or sodium hydroxide when necessary. The KU 10,001 was then introduced by sterile filtration into 20 cc injection vials which were then stoppered.

The Chemical Composition of the Liver Extract

The complete chemical composition of the liver extract useful in the present invention is not yet known. Moreover, the identity of the component, or components, responsible for the effective treatment of viral infections and CFS, is not presently known. It is known, however, that the liver extract KU 10,001 produced in accordance with Example I contains about 33 percent by weight of free amino acids and at least five different polypeptides.

A list of the free amino acids, and the amounts present, in KU 10,001 is set forth below in Table 1.

TABLE 1

| Free Amino Acids Present In Liver Extract | |
|---|---|
| Amino Acid | ug/ml |
| Tryptophan | 30.3 |
| Lysine | 91.0 |
| Histidine | 13.8 |
| Aspartic acid | 69.3 |
| Threonine | 240 |
| Serine | 158 |
| Asparagine | 92.5 |
| Glutamic acid | 347 |
| Proline | 597 |
| Glycine | 133 |
| Alanine | 1283 |
| Valine | 931 |
| Methionine | 383 |
| Isoleucine | 945 |
| Leucine | 1979 |
| Tyrosine | 243 |
| Phenylalanine | 521 |
| | 8057 |

In addition to the free amino acids, KU 10,001 contains at least five polypeptides, one of which has been identified as physiologically active. The separation of this physiologically-active polypeptide is set forth in Example III.

Example III

Physically Active Polypeptide Separation

Starting with a preparation of liver crude as described in *Pharmacopia of the United States*, 15th Ed., p. 379, a large excess of acetone was added to precipitate an insoluble fraction which was collected and dissolved in a minimum of water.

Ten ml of this solution was decolorized with 3.0g of ammonia-activated charcoal. The clear solution was passed through a 90×3.5 cm. column packed with a polyacrylamide preparation as described by Hjerten and Mosbach, *Analytical Biochemistry*, 3, 109–118 (1962) and Hjerten, *Archives of Biochemistry and Biophysics*, Suppl. 1, 147–151 (1962), suitable for use as a molecular sieve that excludes (does not retard) molecules with a molecular weight greater than 20,000. The column was eluted with ammonia. Ten ml. fractions were collected, lyophilized, and dry weights determined.

Three peaks were obtained, hereinafter called A, B and C, and the fractions under each peak were combined and lyophilized When tested for potentiation of bradykinin action on isolated guinea pig ileum, the center peak (B) had most of the bradykinin-potentiating activity.

The combined fractions of peak B were dissolved in water and further purified by ion exchange chromatography on columns of diethylaminoethyl cellulose. Ten mg. of the partially purified product was applied to 35×0.9 cm. columns packed with diethylaminoethyl cellulose (0.9 milli-equiv. capacity). The column was eluted using a gradient that increased the pH in a linear manner from pH 7 to 9. Then sodium chloride was added to increase the sodium chloride concentration in a linear manner to 1 molar sodium chloride. Three peaks (B-1, B-2, B-3) were isolated as the pH was increased from 7 to 9. A fourth peak (B-4) was eluted with the salt gradient at pH 10. Fractions under each peak were collected, lyophilized, and tested for bradykinin-enhancing activity on isolated guinea pig ileum strips. The material in the third peak (B-3) was found to possess high bradykinin-potentiating activity, as demonstrated by the enhancement of bradykinin-induced contractions of guinea pig ileum strips. Also the $A_{280}$ of the material under peak B-3 indicated that it was a polypeptide.

Physical and Chemical Tests on Physiologically Active Polypeptide

Molecular Size—An estimate of the molecular size of the bradykinin-potentiating fraction B-3 was obtained from its behavior in molecular-sieve chromatography experiments. The active material was not retarded on a polyacrylamide preparation (see Hjerten and Mosbach supra, and Hjerten, supra) that excludes, and therefore does not retard, those molecules with a molecular weight above 1,600, suggesting that the molecular weight was greater than 1,600. The active material was retarded on a polyacrylamide preparation (see Hjerten and Mosbach, supra, and Hjerten, supra) that excludes molecules with a molecular weight greater than 4,000, suggesting the molecular weight was less than 4,000. Thus, the results from molecular sieve experiments indicate the molecular weight is less than about 4,000.

Thus, the physiologically-active polypeptide may be characterized by its physical and chemical properties. The active polypeptide is insoluble in acetone, and soluble in water. It has a molecular weight as determined by molecularsieve chromatography experiments to be less than about 4,000.

ADMINISTRATION OF LIVER EXTRACT

The acetone-insoluble liver extract useful in the present invention preferably is administered by injection, for example, intramuscular injection. However, other forms of administration are contemplated.

The liver extract may be employed in the form of pharmaceutically-acceptable salts of the components, such as the alkali metal salts. The pharmaceutically-acceptable amides, lower alkyl esters, protected derivatives, other derivatives and analogues of the components of the liver extract are also contemplated.

Although, as indicated, the liver extract may be used as a water solution, it may also be utilized in association with other pharmaceutical carriers, for example, in saline solution. In any case, since the liver extract is preferably administered by injection, it is contemplated that the extract will be contained in a water base carrier. A preferred product is a water solution containing about 2.5% by weight of liver extract solids.

Dosages may vary depending upon the condition of the patient. Generally, however, it has been found that the administration of 2 ml. of KU 10,001 prepared as described in Example I intramuscularly every other day will produce beneficial results in as little as about 2 weeks.

TEST RESULTS

Example IV

In Vitro Test

KU 10,001 prepared according to Example I was tested using the microtiter infection assay system described in *Journal of Clinical Microbiology*, p. 231–235, Feb. 1968. Briefly, 100 microliters of KU 10,001 in growth medium (RPMI 1640 containing 16% fetal calf serum and 50 ug gentamicin per ml.) at various concentrations were added to the wells of a microtiter plate. MT-2 cells in 100 microliters of growth medium were added to give $3-4 \times 10^4$ cells per well. The plates were incubated for 4 hours at 36° C. in 5% $CO_2$ in air and 100% humidity. Then 50 microliters of HIV-1 virus containing $5-25 \times 10^4$ infectious particles were added to each well. The plates were incubated 3-5 days at 36° C. in 5% $CO_2$ in air and 100% humidity. The MT-2 lymphoblastoid cell line is a human T-cell lymphotropic virus I-transformed T4−T-lymphoblastoid cell line.

To assess culture viability and efficacy of treatment, 100 microliters of each test culture were then transferred to poly-L-lysine-coated wells in a new microtiter plate, and 100 microliters of 0.014% Finter neutral red in growth medium was added to each well. The plates were incubated for 1 hour at 36° C., at which time the medium was removed, and the adhered cells were washed twice with 150 microliters of phosphate buffered saline. The dye was extracted from the adhered cells by adding 100 microliters of acidified alcohol (50% ethanol in 1% acetic acid), and the absorbance of the extracted dye solution at 540nm was measured.

The results of this assay are shown in FIG. 1 which shows that KU 10,001 produced up to 42% cell protection from the cytotoxic effects of HIV-1 on the fourth day after HIV-1 was added to cultures of MT-2. This is a significant anti-HIV effect of the KU 10,001 liver extract and is comparable to that produced by other anti-HIV drugs such as AZT, ddCyd, rIFN-alpha, rIFN-beta, dsRNA, and amphotericin B.

Example V

In Vitro Test

Preliminary results indicated that the phenol at the concentrations present in the in vitro testing of KU 10,001 described in Example IV exhibited cytotoxic effects on the MT-2 cells and that the phenol had no significant antiviral activity. To assess whether this cytotoxic activity was obscuring the antiviral activity of KU 10,001, the following materials were prepared and tested in the microtiter infection assay described in the Example IV:

1. KU 10,001 (prepared as described in Example I).
2. KU 10,004-2 which was prepared by diluting KU 10,004-1 1:3 with water. KU 10,004-1 was prepared by extracting KU 10,000 twice with equal volumes of ethyl ether to remove the phenol. The final aqueous phase is KU 10,004-1 which has a concentration of 80 mg. solids/ml. solution. Thus, KU 10,004-2 has a concentration of 26.7 mg. solids per ml.
3. KU 10,006 which was prepared by precipitating KU 10,000 with 3.8 volumes of acetone to remove the phenol, recovering and drying the precipitate, and dissolving the precipitate in water at 55 mg. solids/ml. solution.

The results of the microtiter assay are shown in Table 2.

TABLE 2

| Dilution | % Cell Survival | | |
|---|---|---|---|
| | KU 10,001 | KU 10,004-2 | KU 10,006 |
| 1:40 | 14.0 | 55.6 | 48.7 |
| 1:80 | 32.7 | 73.8 | 82.0 |
| 1:160 | 30.6 | 77.4 | 105.7 |
| 1:320 | 14.2 | 30.1 | 111.8 |
| 1:640 | 0.3 | 7.4 | 100.8 |
| 1:1280 | −7.6 | 1.6 | 87.1 |

TABLE 2-continued

| Dilution | % Cell Survival | | |
|---|---|---|---|
| | KU 10,001 | KU 10,004-2 | KU 10,006 |
| 1:2560 | −12.4 | −2.0 | 27.2 |
| 1:5120 | −10.7 | 0.2 | 0.0 |

These results show that removal of the phenol substantially improved the ability of the MT-2 in vitro assay to detect the antiviral activity of liver extract.

Example VI

In Vitro Test

A comparison was made of the activity of KU 10,004-1, KU 10,004-2, AZT, ampligen and castanospermine in the microtiter infection assay described in Example IV.

Ampligen $((rI_n)Xr(C_{12}, U)_n)$ is a mispaired doubles-tranded RNA that triggers the induction of human inteferon and has anti-HIV-1 activity Montefiori and Mitchell, Proc. Nat'l Acad. Sci. U.S.A., 84(9), 2985-89 (May 1987).

Castanospermine has the following formula:

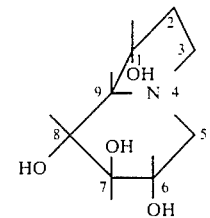

Castanospermine

It is extracted from the seeds of a leguminous tree, *Castanospermum australe*. Castanospermine also has anti-HIV-1 activity.

The various materials listed above were serially diluted and tested in the microtiter infection assay described in Example IV. The starting (undiluted) solution of each material had the following concentration:

| Material | Concentration of Starting Solution (ug/ml) |
|---|---|
| AZT | 0.668 |
| Ampligen | 200 |
| Castanospermine | 118 |
| KU 10,004-1 | 3825 |
| KU 10,004-2 | 1275 |

The results of the assay of these materials in the microtiter infection assay are shown in FIG. 2. As is apparent from FIG. 2, KU 10,004-1 and KU 10,004-2 gave significant cell protection activity comparable to that of AZT and ampligen and better cell protection than castanospermine.

Example VII

In Vivo Test

A group of 131 patients suffering from CFS were treated with KU 10,001 prepared as described in Example I. The patients used in the study were diagnosed as having CFS because they satisfied the criteria described in *Ann. Int. Medicine*. 108:387 (1988).

Before beginning the treatment, numerous laboratory tests were performed including a test for IgG antibodies to Epstein-Barr virus early antigen (EA). The presence of antibodies to EA indicates the presence of an active Epstein-Barr infection. The number of patients in the study group testing positive (i.e., had a titer of 1:80 or greater) for antibodies to EA are shown in Table 3.

The patients were injected intramuscularly with 2 ml. of KU 10,001 every other day. The total number of injections given to each patient varied.

The patients were asked to rate their improvement as either: 1) no improvement; 2) slight improvement; 3) moderate improvement; 4) notable improvement; or 5) marked improvement. The results of these ratings are given in Table 3. Table 3 also gives the average total number of injections given to each group of patients.

TABLE 3

| Rating | Number of Patients | Number of Patients Positive For EA | Average Total Number of Injections |
|---|---|---|---|
| No improvement | 8 | 6 | 11.0 |
| Slight improvement | 11 | 8 | 10.9 |
| Moderate improvement | 19 | 17 | 19.8 |
| Notable improvement | 39 | 21 | 18.1 |
| Marked improvement | 54 | 36 | 16.5 |

As shown in Table 3, treatment of patients diagnosed as having CFS with KU 10,001 resulted in at least a slight improvement in the condition of 94% of the patients. A very substantial number of patients (71%) showed notable or marked improvement.

GENERAL REMARKS

The above disclosure sets forth what the inventors believe is a unique and hitherto unknown method of treating mammals, including humans, infected with virus or suffering from CFS by using a liver extract. The action of the liver extract may be the result of direct virucidal or virustatic activity or may be the result of modulation of the immune response.

At this time it is not known what component, or components, in the liver extract is, or are, responsible for its activity. It is possible the results may be caused by a combination of components.

The KU 10,001 liver extract of Example I has a long history demonstrating lack of toxicity, and a long clinical experience in treating dermatologic conditions. These constitute a distinct advantage over other antivirus drugs, many of which suffer from very serious toxicity.

Although the invention has been described primarily in connection with special and preferred embodiments, it will be understood that it is capable of modification without departing from the scope of the invention. The following claims are intended to cover all variations, uses, or adaptations of the invention, following, in general, the principles thereof and including such departures from the present disclosure as come within known or customary practice in the field to which the invention pertains, or as are obvious to persons skilled in the field.

We claim:

1. A method of treating chronic fatigue syndrome which comprises administering to a person suffering from this syndrome a therapeutically-effective amount of a mammalian liver extract which is referred to herein as KU 10,001, the extract being characterized by being heat stable, insoluble in acetone and soluble in water.

2. The method of claim 1 wherein the liver extract is contained in a pharmaceutically-acceptable carrier at a concentration of about 2.5% by weight solids.

3. The method of claim 2 wherein the liver extract is contained in a pharmaceutically-acceptable carrier at a concentration of about 2.5% by weight solids.

4. The method of claim 3 wherein the liver extract is contained in water.

* * * * *

UNITED STATES PATENT AND TRADEMARK OFFICE
CERTIFICATE OF CORRECTION

PATENT NO. : 5,055,296
DATED : October 8, 1991
INVENTOR(S) : Sudhakar S. Wagle et al.

It is certified that error appears in the above-identified patent and that said Letters Patent is hereby corrected as shown below:

On title page, item [56]
IN THE REFERENCES CITED

On page 1, please delete "3,788,510" and substitute therefor --3,778,510--; and delete "Pltonikoff" and substitute therefor --Plotnikoff--.

IN OTHER PUBLICATIONS

On page 2, column 1, line 30, please delete "Venerial" and substitute therefor --Venereal--.

On page 2, column 1, line 32, before "255" please insert --13--.

On page 2, column 1, line 39, please delete "Veneral" and substitute therefor --Venereal--.

On page 2, column 2, line 8, before "1987" please delete "-".

In column 1, lines 11 and 12, after "extract" please insert --.--.

UNITED STATES PATENT AND TRADEMARK OFFICE
CERTIFICATE OF CORRECTION

PATENT NO. : 5,055,296

DATED : October 8, 1991

INVENTOR(S) : Sudhakar S. Wagle et al.

Page 2 of 4

It is certified that error appears in the above-identified patent and that said Letters Patent is hereby corrected as shown below:

In column 1, line 31, please delete "anti-viral" and substitute therefor --antiviral--.

In column 2, line 3, please delete "Contral" and substitute therefor --Control--.

Column 2, lines 13 and 14, after "acyclovir" insert --.--.

Column 2, line 33, after "activity" insert --.--.

Column 2, line 48, delete "invitro" and substitute therefor --in vitro--.

Column 2, line 52, delete "invitro" and substitute therefor --in vitro--.

In column 3, line 30, after "material" please insert --.--.

UNITED STATES PATENT AND TRADEMARK OFFICE
CERTIFICATE OF CORRECTION

PATENT NO. : 5,055,296
DATED : October 8, 1991
INVENTOR(S) : Sudhakar S. Wagle et al.

It is certified that error appears in the above-identified patent and that said Letters Patent is hereby corrected as shown below:

In column 3, line 38, after "solution" please insert --.--.

In column 4, line 45, please delete "Th®" and substitute therefor --The--.

In column 7, line 11, please delete "T4-T-lymphoblastoid" and substitute therefor --T4+T-lymphoblastoid--.

In column 7, line 20, after "saline" please insert --.--.

In column 7, line 37, please delete "in vitro" and substitute therefor --*in vitro*--.

In column 7, line 40, after "activity" please insert --.--.

In column 8, line 9, please delete "in vitro" and substitute therefor --*in vitro*--.

UNITED STATES PATENT AND TRADEMARK OFFICE
CERTIFICATE OF CORRECTION

PATENT NO. : 5,055,296

DATED : October 8, 1991

INVENTOR(S) : Sudhakar S. Wagle et al.

It is certified that error appears in the above-identified patent and that said Letters Patent is hereby corrected as shown below:

In column 8, line 21, please delete "inteferon" and substitute therefor --interferon--.

Signed and Sealed this

Sixteenth Day of November, 1993

Attest:

BRUCE LEHMAN

Attesting Officer

Commissioner of Patents and Trademarks